US008084661B2

(12) United States Patent
Cross, Jr.

(10) Patent No.: US 8,084,661 B2
(45) Date of Patent: Dec. 27, 2011

(54) EXTRACTION OF ASO FROM SPENT SULFURIC ACID USING LIQUID $SO_2$

(75) Inventor: William M. Cross, Jr., Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 579 days.

(21) Appl. No.: 12/334,009

(22) Filed: Dec. 12, 2008

(65) Prior Publication Data

US 2010/0152517 A1 Jun. 17, 2010

(51) Int. Cl.
*C07C 2/00* (2006.01)
*C07C 2/16* (2006.01)
*B01J 20/34* (2006.01)

(52) U.S. Cl. ........ 585/709; 585/721; 585/730; 585/731; 502/22; 502/24; 502/28; 502/36; 502/517

(58) Field of Classification Search ............ 585/530, 585/531, 700, 704, 721, 731; 379/68
See application file for complete search history.

(56) References Cited

U.S. PATENT DOCUMENTS

| | | | |
|---|---|---|---|
| 2,415,003 A * | 1/1947 | Cole | ............................ 585/723 |
| 2,716,592 A | 8/1955 | Skelly et al. | |
| 2,762,853 A | 9/1956 | Jones et al. | |
| 2,859,260 A | 11/1958 | Stiles | |
| 2,881,058 A | 4/1959 | Atteridg | |
| 3,227,775 A | 1/1966 | Goldsby | |
| 3,534,118 A | 10/1970 | Massa | |
| 3,607,035 A | 9/1971 | Jones | |
| 3,652,708 A * | 3/1972 | Lewis et al. | .................. 423/527 |
| 3,663,648 A | 5/1972 | Ruble | |
| 3,673,271 A | 6/1972 | Goldsby | |
| 4,071,576 A * | 1/1978 | Behrmann et al. | ............ 585/704 |
| 4,073,821 A * | 2/1978 | Siskin | ........................... 585/718 |
| 4,479,926 A * | 10/1984 | Behrmann et al. | ............ 423/467 |
| 5,730,843 A | 3/1998 | Groten et al. | |
| 6,000,684 A | 12/1999 | Pasch et al. | |
| 6,774,275 B2 | 8/2004 | Smith, Jr. et al. | |

FOREIGN PATENT DOCUMENTS

GB 1300835 12/1972

* cited by examiner

*Primary Examiner* — In Suk Bullock
*Assistant Examiner* — Donald Payne
(74) *Attorney, Agent, or Firm* — Osha • Liang LLP (57) ABSTRACT

A process for the regeneration of spent sulfuric acid including contacting spent sulfuric acid containing acid soluble oils (ASO) with sulfur dioxide to extract at least a portion of the ASO from the spent sulfuric acid into the sulfur dioxide. The sulfuric acid phase having a reduced ASO content and a sulfur dioxide phase containing at least a portion of the ASO may be recovered. The resulting sulfuric acid and sulfur dioxide phases may be further separated to recover ASO, sulfur dioxide, and sulfuric acid.

19 Claims, 5 Drawing Sheets

EXTRACTION OF ASO FROM SPENT SULFURIC ACID USING LIQUID $SO_2$

BACKGROUND OF DISCLOSURE

1. Field of the Disclosure

Embodiments disclosed herein relate generally to regeneration of sulfuric acid. More specifically, embodiment disclosed herein relate to extraction of ASO (acid soluble oils) to regenerate spent sulfuric acid. In particular, embodiments disclosed herein relate to using $SO_2$ (sulfur dioxide) to extract ASO from spent sulfuric acid.

2. Background

Concentrated sulfuric acid is a strong Bronsted acid used in a variety of chemical processes to promote acid catalyzed reactions. In particular, sulfuric acid is commonly utilized in alkylation of isoparaffins and olefins for the production of motor fuel alkylate.

In a typical alkylation process, the reaction is carried out in a reactor where the hydrocarbon reactants are dispersed into a continuous acid phase. For example, U.S. Pat. No. 2,762,853 discloses an alkylation process including feeding isoparaffins, such as isobutane or isopentane and $C_2$-$C_5$ monoolefins to an alkylation reactor. The alkylation reaction is catalyzed with sulfuric acid in excess of 88 percent, preferably in excess of 96 percent. The alkylation products are then separated into gasoline range components and heavier alkylate products, among other finishing processes.

As another example, U.S. Pat. No. 2,859,260 discloses an alkylation process including reacting isoparaffins with olefins in the presence of a sulfuric acid catalyst. The reaction product is then separated to recover a hydrocarbon-rich phase and an acid-rich phase. The hydrocarbon-rich phase is further treated to remove catalyst esters from the hydrocarbon phase, among other downstream operations.

All such processes produce a spent acid stream of reduced acid concentration containing a variety of heavy organic compounds that are soluble in the acid, commonly referred to as "acid soluble oils," or ASO. ASO includes constituents which stay in the sulfuric acid phase upon contacting high strength acid (>80% wt) with hydrocarbon unsaturates. This includes components such as alkyl sulfates (also referred to as mono alkyl sulfates or mono esters), dialkyl sulfate (diesters) which are formed during an alkylation process, and constituents termed conjunct polymers, as described in "Molecular Structure of Conjunct Polymers" by Miron & Lee, Journal of Chemical Engineering, Vol. 8, No. 1, January 1963. Due to recycle and reuse of sulfuric acid in the alkylation process, the concentration of ASO in the spent sulfuric acid builds up over time, requiring regeneration of the spent sulfuric acid.

One process for regenerating spent sulfuric acid streams, as disclosed, for example, in British Patent No. 1,300,835 involves (a) introducing the spent acid into a furnace fired by an air/hydrocarbon fuel mixture wherein the spent acid is converted to sulfur dioxide, water, and carbon dioxide, (b) partially cooling the combustion gas in a waste heat boiler, (c) treating the gas to remove particulates, (d) converting the sulfur dioxide in the gas to sulfur trioxide (by reaction with oxygen in the gas stream) in a fixed bed reactor system containing a vanadium catalyst with or without pretreatment to remove the water contained in the gas stream, and (e) recovering the sulfur trioxide as concentrated sulfuric acid via absorption in dilute sulfuric acid or direct condensation if water is present in the gas stream. The vent gas, after treatment to remove acid mist, generally contains carbon dioxide, oxygen, nitrogen, and a small amount of residual sulfur dioxide.

Other currently known methods for regeneration of sulfuric acid include (a) production of alkyl sulfates or di-alkyl sulfates and their recovery, as disclosed, for example, in U.S. Pat. Nos. 3,534,118; 3,663,648; and 3,673,271; (b) extraction with propane, as disclosed, for example, in U.S. Pat. No. 3,227,775; (c) sulfuric acid crystallization, as disclosed, for example, in U.S. Pat. Nos. 2,716,592 and 2,881,058; and (d) benzene extraction, as disclosed, for example, in U.S. Pat. No. 3,607,035.

For a small operator, the amount of spent acid produced may not be sufficient to justify installation of an onsite conventional acid regeneration facility. Further, sulfuric acid disposal via direct incineration as described above may not be desirable due to increased emissions. The alternative is to ship the spent acid to a large scale sulfuric acid plant serving multiple spent acid generators and to receive purified acid in exchange. However, this alternative may not be particularly attractive when compared to the cost of fresh acid.

Accordingly, there exists a need for additional methods for regenerating spent sulfuric acid that are both economically-feasible and environmentally-acceptable.

SUMMARY OF THE DISCLOSURE

In one aspect, embodiments disclose herein relate to a process for regeneration of sulfuric acid, including: contacting a spent sulfuric acid comprising sulfuric acid and acid soluble oils with sulfur dioxide, wherein at least a portion of the acid soluble oils partitions into the sulfur dioxide; recovering an extract fraction comprising the sulfur dioxide and at least a portion of the acid soluble oils; and recovering a raffinate fraction comprising the spent sulfuric acid, having a reduced content of the acid soluble oils.

In another aspect, embodiments disclosed herein relate to an alkylation process, including: contacting olefins and paraffins with sulfuric acid in an alkylation reaction zone; recovering an alkylate product from the alkylation reaction zone; recovering a spent sulfuric acid comprising sulfuric acid and acid soluble oils from the alkylation reaction zone; contacting at least a portion of the spent sulfuric acid with sulfur dioxide in an extraction zone, wherein at least a portion of the acid soluble oils partitions into the sulfur dioxide; recovering an extract fraction comprising the sulfur dioxide and at least a portion of the acid soluble oils from the extraction zone; recovering a raffinate fraction comprising the spent sulfuric acid, having a reduced content of acid soluble oils, from the extraction zone; separating the extract fraction in a first separation zone to recover a first sulfur dioxide fraction and an acid soluble oils fraction; and separating the raffinate fraction in a second separation zone to recover a second sulfur dioxide fraction and a sulfuric acid fraction.

Other aspects and advantages will be apparent from the following description and the appended claims.

DETAILED DESCRIPTION

In one aspect, embodiments disclosed herein relate to a process for regenerating spent sulfuric acid by removing the ASO (acid soluble oils) dissolved in the spent sulfuric acid. More particularly, embodiments disclosed herein relate to a process of using sulfur dioxide to extract ASO from spent sulfuric acid.

It has been found that ASO may be effectively and efficiently extracted from spent sulfuric acid stream using liquid sulfur dioxide. For example, spent sulfuric acid including ASO from an alkylation unit may be contacted with liquid $SO_2$, whereby at least a portion of the ASO partitions into the $SO_2$ phase. The resulting phase, including $SO_2$ and ASO, may then be separated, and the $SO_2$ may be recycled to the extraction step. Trace amounts of $SO_2$ may also be dissolved in the recovered acid phase, which may be separated from the sulfuric acid. The recovered sulfuric acid fraction may then be re-used in the alkylation process. Alternatively, additional acid strength may be attained prior to acid recycle via combustion of $SO_2$ to $SO_3$, and reacting the $SO_3$ with any water in the sulfuric acid. The $SO_3$ in combination with any water present may result in an acid having an increased strength for recycling to alkylation.

Figure 1:
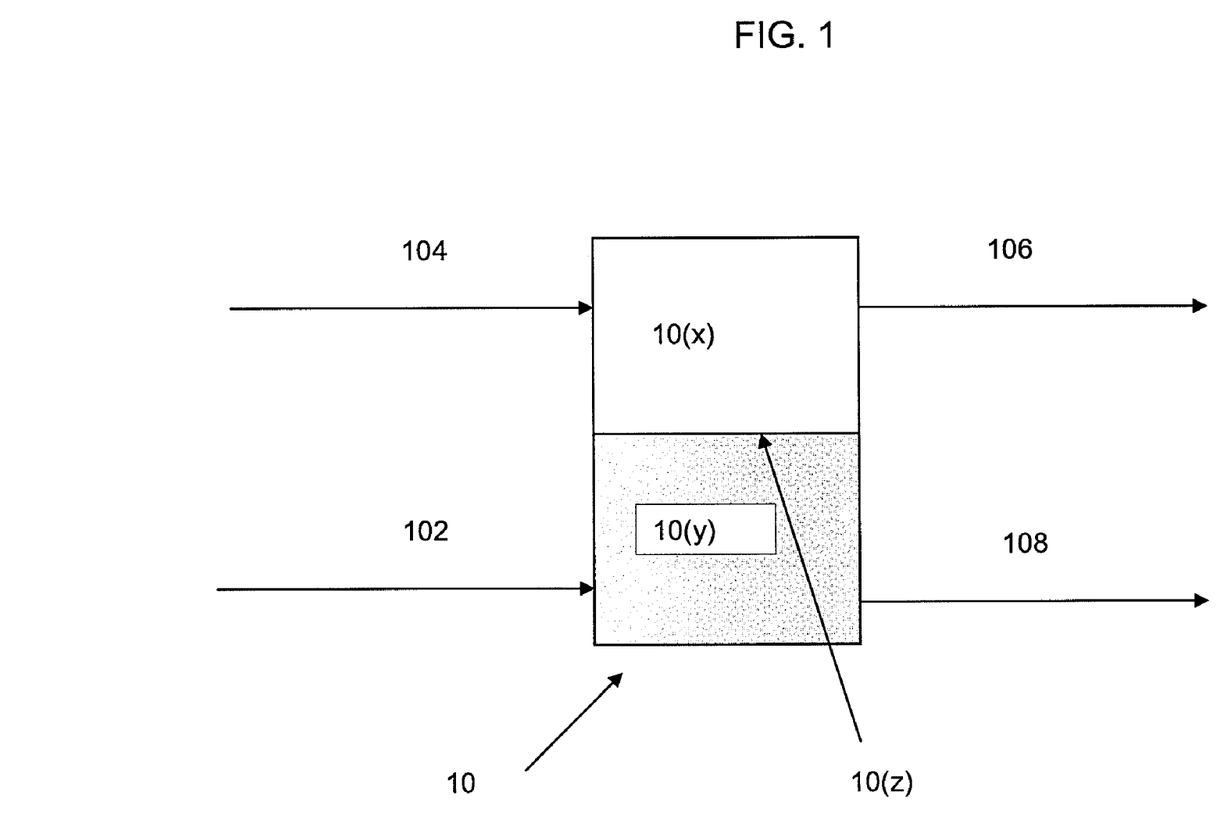
FIG. 1 is a simplified flow diagram of a process for extracting ASO from spent sulfuric acid using sulfur dioxide according to embodiments disclosed herein.

Referring now to FIG. 1, a process for regeneration of spent sulfuric acid according to embodiments disclosed herein is illustrated. Spent sulfuric acid containing sulfuric acid and acid soluble oils (ASO) may be fed to extraction zone 10 at a single or multiple locations via flow line 102. Sulfur dioxide may be fed to extraction zone 10 at a single or multiple location via flow line 104. In one embodiment, the spent sulfuric acid and the sulfur dioxide may be pre-mixed and fed to extraction zone 10 via a single flow line. Conditions in extraction zone 10 may be maintained such that the sulfur dioxide is a liquid during the extraction process.

The spent sulfuric acid feed in flow line 102 may contain some water. In some embodiments, the spent sulfuric acid may have a water content of less than approximately 5 weight percent. In other embodiments, the spent sulfuric acid may have a water content of less than approximately 4 weight percent. In other embodiments, the spent sulfuric acid may have a water content of less than approximately 3 weight percent. In yet other embodiments, the spent sulfuric acid may have a water content of less than approximately 2.5 weight percent. In yet other embodiments, the spent sulfuric acid may have a water content of less than approximately 2 weight percent. In yet other embodiments, the spent sulfuric acid may have a water content of less than approximately 1.5 weight percent. In still other embodiments, the spent sulfuric acid may have a water content of less than approximately 1 weight percent.

Similarly, the sulfur dioxide in flow line 104 may contain some water and other impurities. In some embodiments, the sulfur dioxide may have a water content of less than approximately 5 weight percent. In other embodiments, the sulfur dioxide may have a water content of less than approximately 4 weight percent. In other embodiments, the sulfur dioxide may have a water content of less than approximately 3 weight percent. In yet other embodiments, the sulfur dioxide may have a water content of less than approximately 2.5 weight percent. In yet other embodiments, the sulfur dioxide may have a water content of less than approximately 2 weight percent. In yet other embodiments, the sulfur dioxide may have a water content of less than approximately 1.5 weight percent. In still other embodiments, the sulfur dioxide may have a water content of less than approximately 1 weight percent.

The spent sulfuric acid and the sulfur dioxide may be contacted in extraction zone 10 as two immiscible phases: sulfur dioxide phase 10(x) and spent sulfuric acid phase 10(y). In one embodiment, the sulfur dioxide and the spent sulfuric acid may form a two-phase immiscible liquid-liquid system During contact of the two phases, at least a portion of the ASO may be extracted from the spent sulfuric acid phase 10(y) into the sulfur oxide phase 10(x). For example, the ASO may initially be dissolved in spent sulfuric acid feed 102. Upon contact with sulfur dioxide feed 104, at least a portion of the ASO dissolved in sulfuric acid phase 10(y) may partition into sulfur dioxide phase 10(x) across interface 10(z).

In some embodiments, the regeneration of spent sulfuric acid according to embodiments disclosed herein may be conducted in a single extraction stage. In other embodiments, the regeneration of spent sulfuric acid according to embodiments disclosed herein may be conducted in two or more extraction stages. For example, the extract fraction in flow line 106 and the raffinate fraction in flow line 108 may each be fed to another extraction zone for further processing.

Each of the one or more extraction stages for regeneration of the spent sulfuric acid using the sulfur dioxide may include a contact structure in order to enhance the contact efficiency of the two phases. For example, contact structures including any type of device or structure commonly used for contacting two liquids or for contacting vapors and liquids, including agitated vessels, static mixers, trickle beds, and other structures known in the art may be used. Contacting structures may also include disperser material, such as random or dumped distillation packings, structured packings, and multi filament elements, e.g., knit wire. Other types of contact structures may also be used, such as those described in U.S. Pat. Nos. 6,774,275; 5,730,843; and 6,000,684, which are incorporated herein by reference.

In one embodiment, a contact structure for contacting the spent sulfuric acid and the sulfur dioxide may be a mixer-settler stage. For example, partitioning of the ASO between two phases may be enhanced by contacting the spent sulfuric acid and the sulfur dioxide in an agitated vessel or in a static mixer. Following the contact, the spent sulfuric acid and the sulfur dioxide may be allowed to settle and separate into a raffinate fraction and an extract fraction based upon their differing densities, for example, using a coalescer, a settling tank, or other suitable means or device. The extract fraction comprising sulfur dioxide and at least a portion of the extracted ASO may be recovered from extraction zone 10 via flow line 106. The raffinate fraction comprising sulfuric acid may be recovered from extraction zone 10 via flow line 108.

Figure 1A:
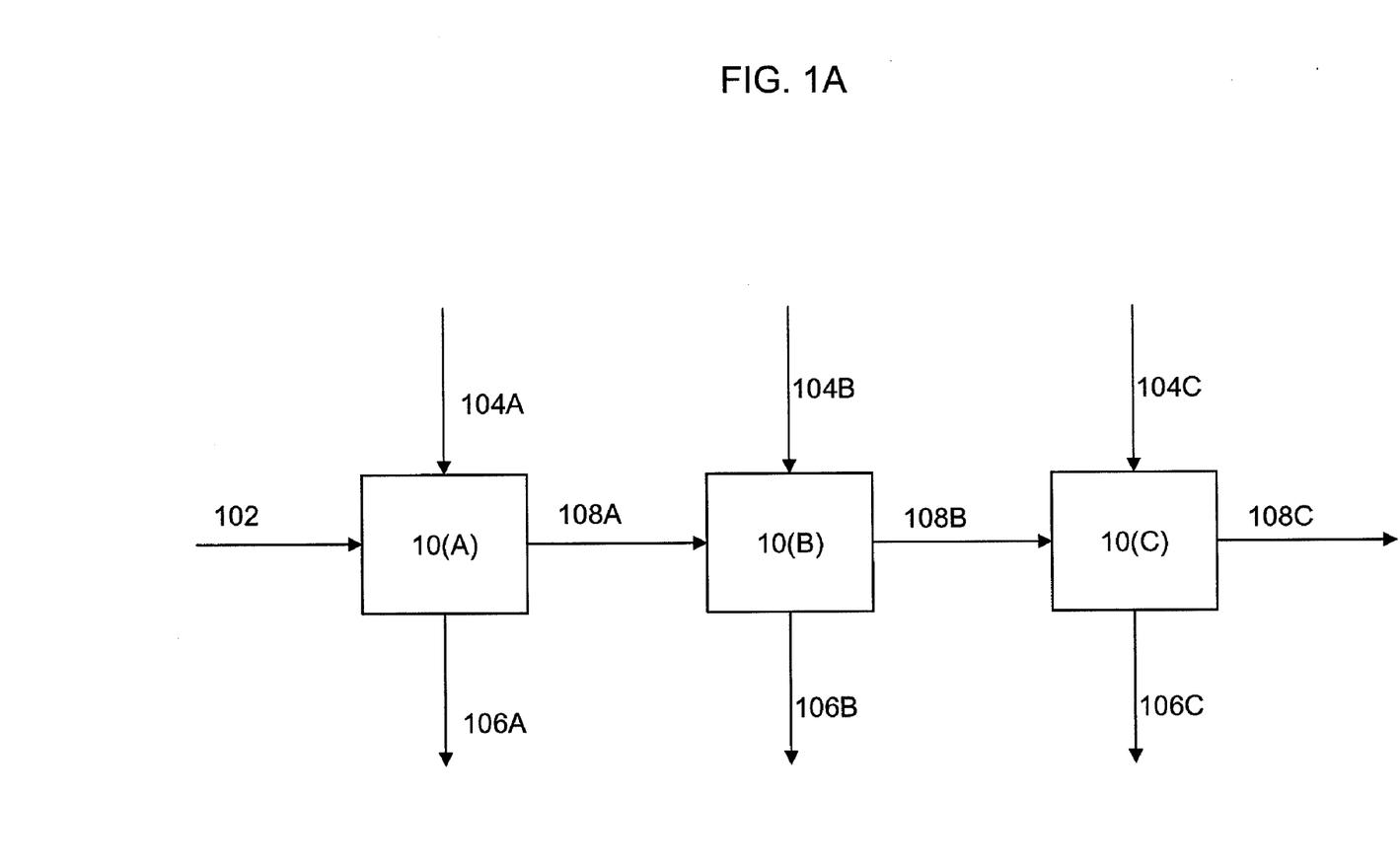
FIG. 1A is a simplified flow diagram of a process for extracting ASO from spent sulfuric acid using sulfur dioxide according to embodiments disclosed herein.
Figure 1B:
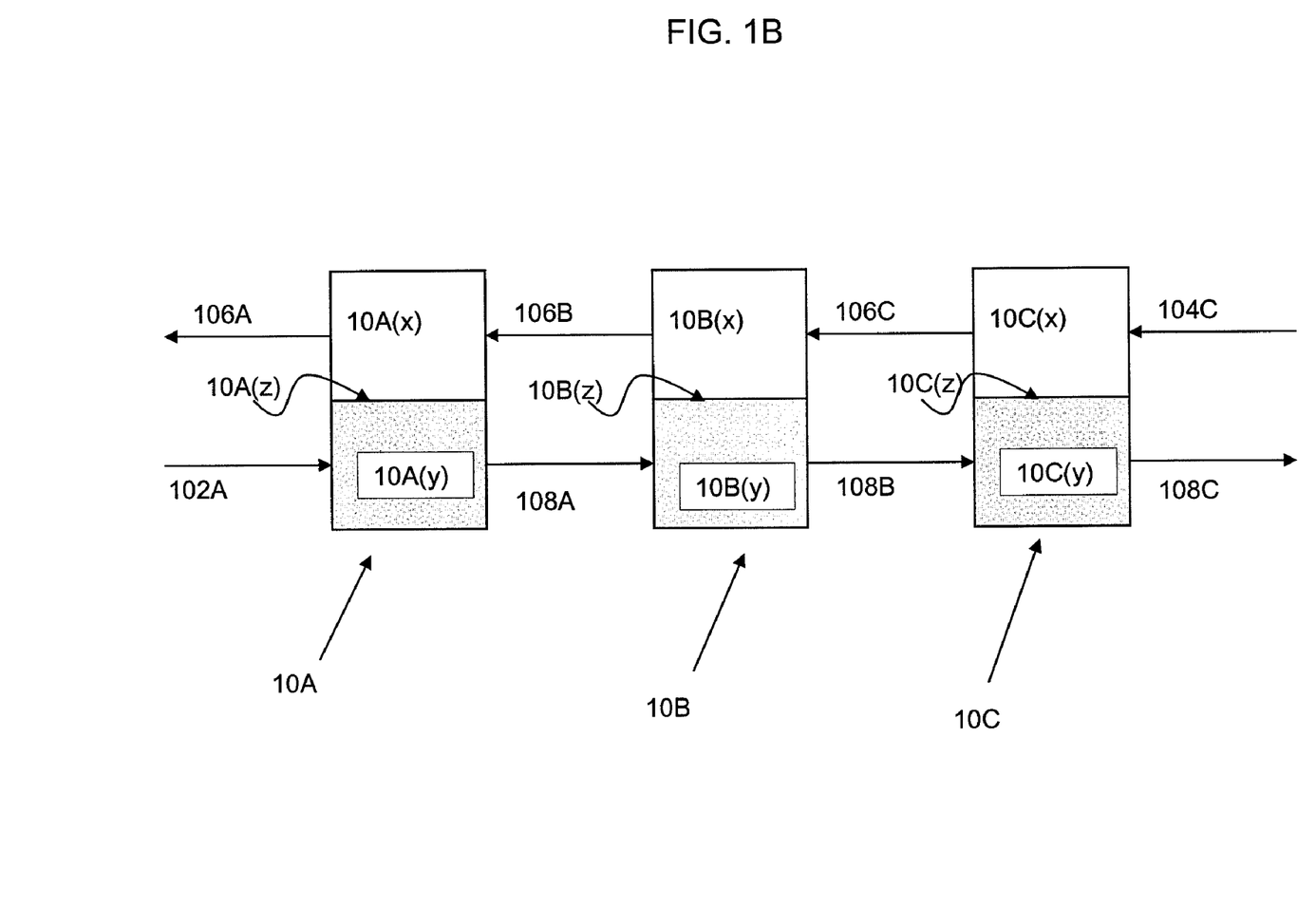
FIG. 1B is a simplified flow diagram of a process for extracting ASO from spent sulfuric acid using sulfur dioxide according to embodiments disclosed herein.

Referring now to FIGS. 1A and 1B, where like numerals represent like parts, processes for regeneration of spent sulfuric acid according to embodiments disclosed herein are illustrated. As shown therein, the spent sulfuric acid containing ASO may be contacted with sulfur dioxide in multiple (i.e., two or more) extraction stages, where the extraction stages may be performed with the sulfur dioxide and spent sulfuric acid feeds contacted using at least one of cross flow or counter-current flow.

Referring to FIG. 1A, the two or more extraction stages may be arranged with the spent sulfuric acid and the sulfur dioxide fed cross-currently. For example, a spent sulfuric acid feed 102 may be fed to a first extraction zone 10A and contacted with sulfur dioxide fed via flow line 10. The ASO extracted into the sulfur dioxide phase in first extraction zone 10A may be recovered as an extract fraction via flow line 106A, and a first raffinate fraction 108A, comprising sulfuric acid and ASO unextracted in first extraction zone 10A, may be fed to second extraction zone 10B, wherein they may be contacted further with fresh SO2 fed via stream 104B to extract at least a portion of the ASO remaining in first raffinate fraction 108A. Second extract fraction 106B having an increased concentration of ASO can be combined with the first extract fraction 106A and sent to an sulfur dioxide recovery section. Likewise, second raffinate fraction 108B, comprising sulfuric acid having a reduced concentration of ASO, may be recovered from second extraction zone 10B and contacted in a third extraction zone 10C with fresh sulfur dioxide fed via stream 104C to form third raffinate fraction 108C, comprising sulfuric acid having a further reduced concentration of ASO, and third extract fraction 106C, having an increased concentration of ASO. Third extract fraction 106C may also be combined with extract fractions 106A and 106B for further processing in a sulfur dioxide recovery section.

Referring to FIG. 1B, the two or more extraction stages may be arranged counter-currently. For example, spent sulfuric acid 102A, containing sulfuric acid and acid soluble oils (ASO), may be contacted in first extraction zone 10A with second extract fraction 106B, containing sulfur dioxide and a portion of ASO extracted in third extraction zone 10C, and then in second extraction zone 10B. Third extract fraction 106A, having an increased concentration of ASO, may be recovered from first extraction zone 10A. First raffinate fraction 108A, comprising sulfuric acid having a reduced concentration of ASO, may be recovered from first extraction zone 10A. First raffinate fraction 108A may then be contacted in second extraction zone 10B with first extract fraction 106C, containing sulfur dioxide and a portion of ASO extracted in third extraction zone 10C. Second raffinate fraction 108B, comprising sulfuric acid having a reduced concentration of ASO, may be recovered from second extraction zone 10B, and may be contacted in third extraction zone 10C with sulfur dioxide 104C.

In a cross flow arrangement, each raffinate fraction may be contacted with a fresh extract fraction having no or very low ASO concentration (depending on the sulfur dioxide recovery section used (see FIG. 1A)).

In contrast, in a counter-current flow arrangement, spent sulfuric acid 102A having the highest ASO feed concentration may be contacted with second extract fraction 106B also having highest ASO feed concentration, and sulfur dioxide 104C having lowest ASO feed concentration may be contacted with second raffinate fraction 108B also having lowest ASO feed concentration (see FIG. 1B). Such an arrangement may be preferred as typically less total SO2 volumetric process flow is required.

Figure 2:
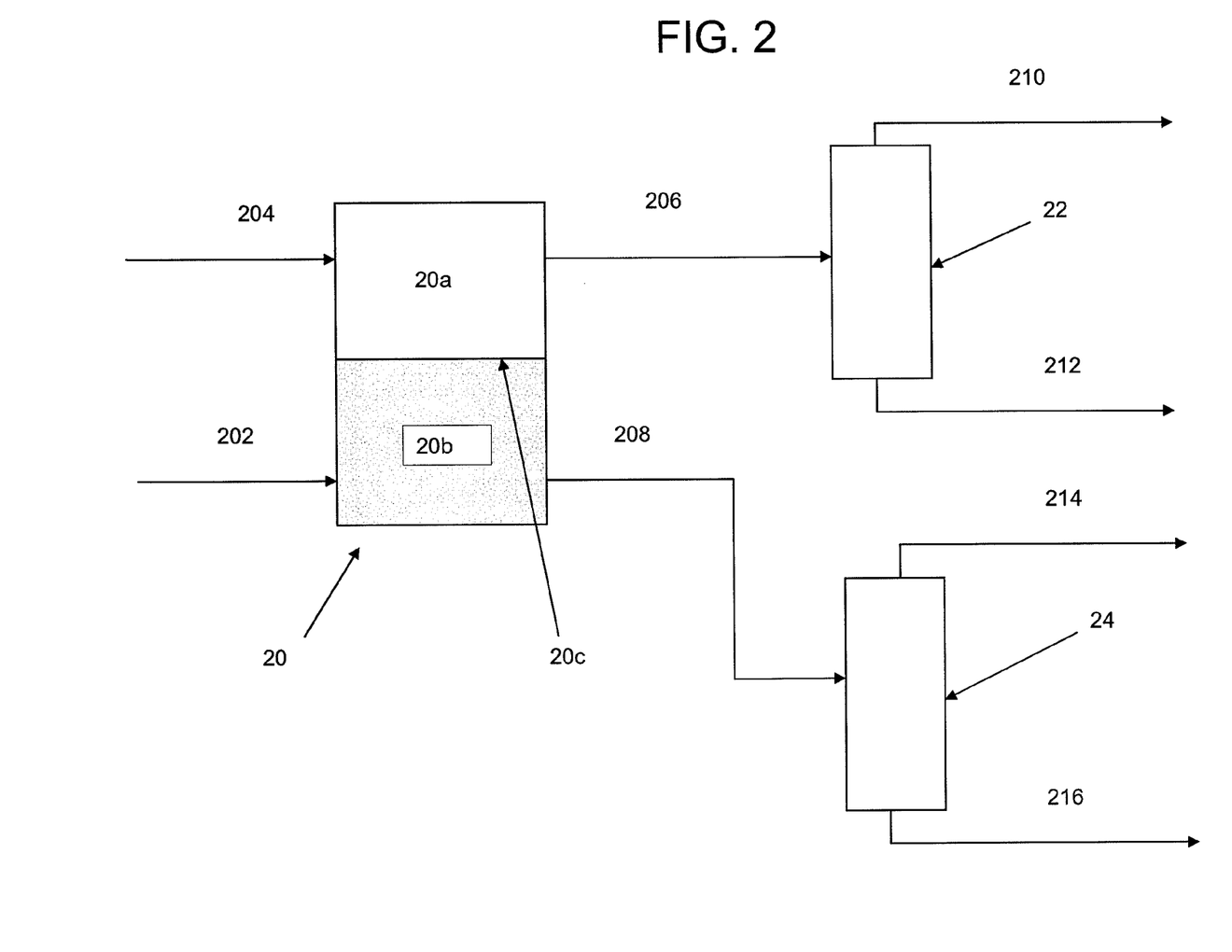
FIG. 2 is a simplified flow diagram of a process for extracting ASO from spent sulfuric acid using sulfur dioxide according to embodiments disclosed herein.

Referring now to FIG. 2, a process for regeneration of spent sulfuric acid according to embodiments disclosed herein is illustrated. Additional steps may be provided for recovery of ASO from the sulfur dioxide fraction and of sulfur dioxide from sulfuric acid fraction resulting from the above described extraction stages.

Spent sulfuric acid containing sulfuric acid and acid soluble oils (ASO) may be fed to an extraction zone 20 at a single or multiple locations via flow line 202. Sulfur dioxide may be fed to extraction zone 20 at a single or multiple location via flow line 204.

An extract fraction comprising sulfur dioxide and at least a portion of the ASO may be recovered from extraction zone 20 via flow line 206. A raffinate fraction comprising sulfuric acid may be recovered from extraction zone 20 via flow line 208.

The extract fraction 206 may be separated in a separation zone 22 to separate ASO from the sulfur dioxide. In some embodiments, separation zone 22 may be a distillation tower comprising at least one of trays and packing. In other embodiments, separation zone 22 may be a stripping tower. Following separation, the ASO may be recovered as bottoms fraction 212 and the sulfur dioxide may be recovered as overheads fraction 210.

During extraction in extraction zone 20, a portion of the sulfur dioxide may dissolve in the spent sulfuric acid. If necessary, raffinate fraction 208 may be fed to separation zone 24 to separate sulfuric acid from the dissolved sulfur dioxide. In some embodiments, separation zone 24 may be a distillation tower comprising at least one of trays and packing. In other embodiments, separation zone 24 may be a stripping tower. Following the separation, the sulfuric acid may be recovered as bottoms fraction 216 and the sulfur dioxide may be recovered as overheads fraction 214.

In some embodiments, it may be beneficial to use the process for regenerating spent sulfuric acid according to embodiments disclosed herein in conjunction with an existing alkylation process. For example, sulfur dioxide may be used to regenerate spent sulfuric acid generated by sulfuric acid catalyzed alkylation processes. Upon contact with sulfuric acid, reactants in the alkylation process, such as paraffins and olefins, may react with sulfuric acid to form ASO as a byproduct, which may subsequently be separated from the spent sulfuric acid as described above. Such a process may be advantageous to a small-scale operator for whom the capital and the operating costs of a large sulfuric acid plant may not be economically feasible.

Figure 3:
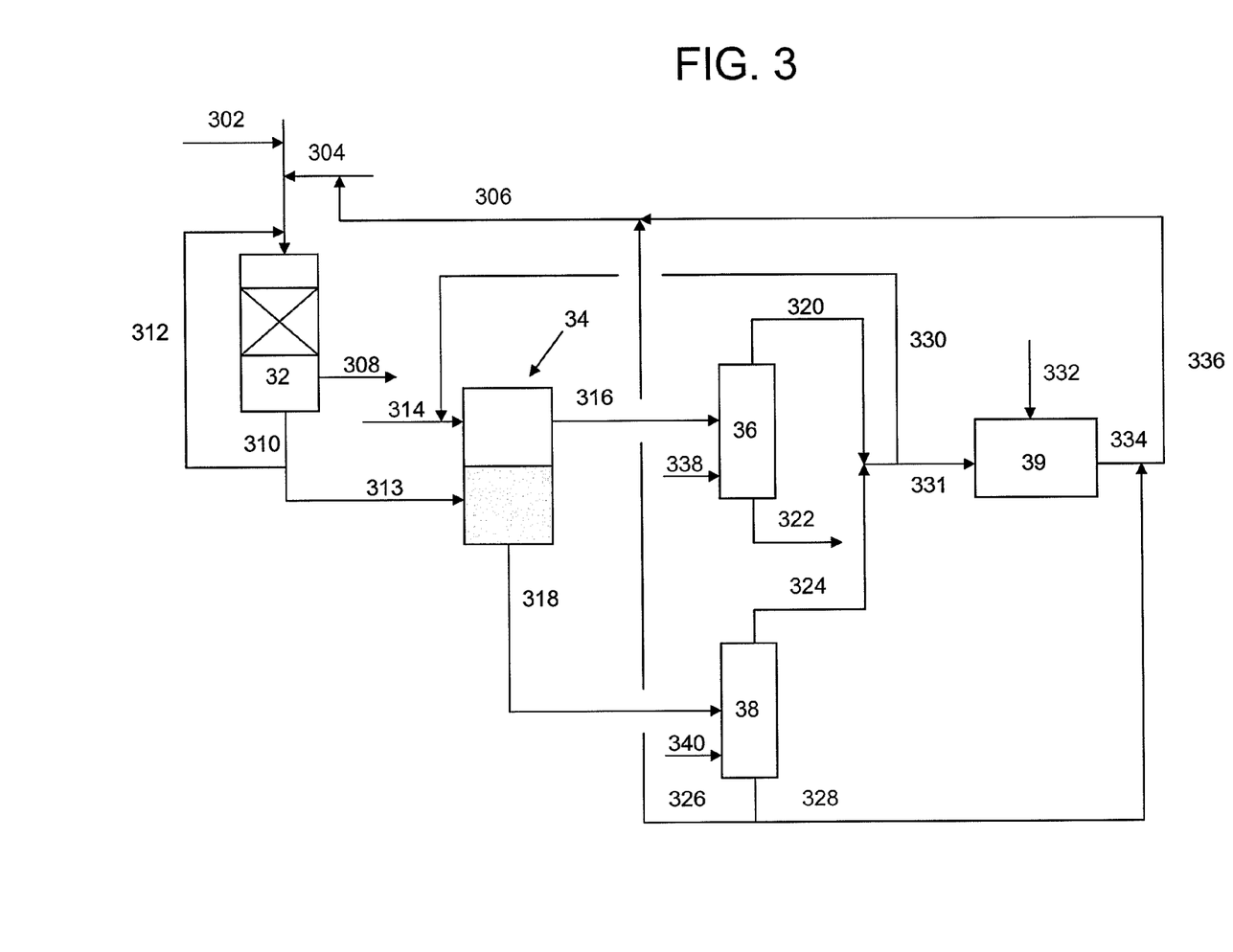
FIG. 3 is a simplified flow diagram of an alkylation process including spent sulfuric acid regeneration according to embodiments disclosed herein.

Referring now to FIG. 3, an alkylation process, including sulfuric acid regeneration according to embodiments disclosed herein, is illustrated. Olefins and paraffins in flow line 302 may be contacted with sulfuric acid in flow line 304 in alkylation reactor 32, which may comprise one or more alkylation reaction zones.

Alkylate product, along with any unreacted olefins and paraffins, may be recovered from alkylation reactor 32 via flow line 308. Spent sulfuric acid along with dissolved ASO byproduct formed in alkylation reactor 32 may be recovered via flow line 310. A portion of spent sulfuric acid 310 may be recycled back to alkylation reactor 32 via flow line 312, and the rest may be fed to extraction zone 34 via flow line 313. Spent sulfuric acid 313 may then be contacted in extraction zone 34 with sulfur dioxide fed via flow line 314. Upon contact with sulfur dioxide 314, at least a portion of the ASO dissolved in spent sulfuric acid 310 may partition into sulfur dioxide 314 across a two-phase interface. An extract fraction comprising sulfur dioxide and ASO may be recovered from extraction zone 34 via flow line 316. A raffinate fraction comprising sulfuric acid may be recovered from extraction zone 34 via flow line 318.

Extract fraction 316 may be fed to separation zone 36 to separate ASO from sulfur dioxide. In some embodiments, separation zone 36 may be a distillation tower comprising at least one of trays and packing. Following the separation, the ASO may be recovered as a bottoms fraction 322 and the sulfur dioxide may be recovered as a overheads fraction 320.

During extraction in extraction zone 34, a portion of the sulfur dioxide may dissolve in the spent sulfuric acid. If necessary, raffinate fraction 318 may be fed to separation zone 38 to separate sulfuric acid from the dissolved sulfur dioxide. Following the separation, the sulfuric acid may be recovered as bottoms fraction 328 and the sulfur dioxide may be recovered as overheads fraction 324. If desired, at least a portion of sulfuric acid in bottoms fraction 328 may be recycled to alkylation reactor 32 via flow line 326. Sulfur dioxide in overheads fraction 320 and overheads fraction 324 may be combined as flow line 331, and a portion of the sulfur dioxide may be recycled to extraction zone 34 via flow line 330.

Typically, the temperature required for regeneration of spent sulfuric acid via sulfur dioxide extraction according to embodiments disclosed herein is much lower than the temperature required for regeneration of sulfuric acid via combustion. In some embodiments, the process for regenerating spent sulfuric acid according to embodiments disclosed herein can be operated at less than approximately 200° F. (93° C.). In other embodiments, the process for regenerating spent sulfuric acid according to embodiments disclosed herein can be operated at less than approximately 150° F. (66° C.). In yet other embodiments, the process for regenerating spent sulfuric acid according to embodiments disclosed herein can be operated at less than approximately 100° F. (38° C.). In one particular embodiment, the process for regenerating spent sulfuric acid according to embodiments disclosed herein can be operated at approximately 77° F. (25° C.).

Further, in at least one of separation zone 36 and separation zone 38, it may be advantageous to limit the operating temperature. For example, reduced operating temperatures may reduce equipment corrosion. If necessary to reduce operating temperatures, an inert gas may be fed to separation zone 36 via flow line 338 and to separation zone 38 via flow line 340. In some embodiments, the inert gas may include at least one of isobutane, propane and nitrogen.

Sulfur dioxide, as described above, may be used to extract the ASO from the spent sulfuric acid. Additionally, sulfur dioxide may also be used to increase the strength of the sulfuric acid. For example, the presence of water and other impurities in the sulfuric acid can reduce the strength, and therefore the effectiveness, of sulfuric acid as an alkylation catalyst. Accordingly, it may be advantageous to increase the strength of the sulfuric acid.

To increase the strength of the acid, at least a portion of the sulfur dioxide 331 may then be reacted in combustion zone 39 in the presence of oxygen 332 and a catalyst to produce sulfur trioxide 334. In some embodiments the catalyst may be a vanadium catalyst.

Combustion of sulfur dioxide to produce sulfur trioxide is an exothermic process. Accordingly, in some embodiments, the sulfuric acid produced by combustion of sulfur dioxide may be at a high temperature. In other embodiments, the sulfuric acid product may be in vapor form. Various methods may be used to cool or condense the sulfuric acid product. In one embodiment, the sulfuric acid may be condensed in a steam boiler, whereby the heat of combustion of sulfur dioxide is absorbed by water in order to produce steam. Thus, one benefit of combusting sulfur dioxide according to embodiments disclosed herein in order to increase the strength of the sulfuric acid is that the heat of combustion may be captured by producing steam for plant use.

Sulfur trioxide 334 may then be contacted with bottoms fraction 328, containing sulfuric acid and water. Upon contact, sulfur trioxide 334 may react with water in bottoms fraction 328 to form additional sulfuric acid. As the result, the concentration of sulfuric acid in bottoms fraction 328 may be increased, as at least a portion of the water impurity is converted into additional sulfuric acid upon contact with sulfur trioxide. Concentrated sulfuric acid 336 may be recycled to alkylation reactor 32. In some embodiments, concentrated sulfuric acid 336 may be combined with sulfuric acid in flow line 326 and recycled to alkylation reactor 32 via flow line 306.

EXAMPLE 1

This example illustrates an embodiment according to the present disclosure as shown in FIG. 1. Spent sulfuric acid was regenerated in a pilot plant alkylation facility by feeding 42.3 grams of spent sulfuric acid to a 6 inch (15 cm) tall stainless steel sight glass containing a glass window, and feeding 39.5 grams of liquid $SO_2$ to the sight glass on top of the acid. The process was operated at a mixture temperature of 77° F. (25° C.) and at a pressure equal to the corresponding vapor pressure of $SO_2$. The spent sulfuric acid and the $SO_2$ fluids were found to be immiscible and formed a phase interface. The $SO_2$ phase was found to be light-yellow and slightly milky in color. The two fluids in the sight glass were then slowly mixed by shaking at low agitation for approximately 10-15 minutes, and then allowed to settle. The resulting $SO_2$ phase was found to be darker, copper-brown in color, indicating that at least a portion of the hydrocarbons from the spent acid had been extracted by the liquid $SO_2$. Approximately two thirds of the volume of acid in the sight glass was collected for analysis (Extract 1). The remaining acid was contacted with an additional 34.4 grams of $SO_2$, mixed for around 10 minutes, and allowed to settle. This final amount of acid was then collected for analysis (Extract 2). The following table shows the analysis of the spent sulfuric acid, as well as Extract 1 and Extract 2:

TABLE 1

Extraction Analysis: Spent Sulfuric Acid Regeneration Process According to Example 1.

| Sample | Acid (weight %) | Water (weight %) |
| --- | --- | --- |
| Spent Sulfuric Acid | 88.88 | 2.39 |
| Extract 1 | 90.06 | 2.40 |
| Extract 2 | 91.21 | 2.65 |

The net composition of the Spent Sulfuric Acid, Extract 1, and Extract 2 accounts for various impurities, including primarily the ASO. It is evident that the strength of the acid has increased following the extraction by over 1 weight percent following the first extraction step, and by a total of over 2 weight percent following the second extraction step. The slight increase in water composition is expected, as the total amount of ASO in the acid is reduced. As the water composition has not significantly changed following the extraction, whereas the composition of the acid has increased, it is evident that at least a portion of the ASO has been extracted into the $SO_2$ phase. Accordingly, this example demonstrates that $SO_2$ can be used effectively to extract ASO from spent sulfuric acid according to embodiments disclosed herein.

Advantageously, using processes according to embodiments disclosed herein may allow for reduced capital cost of regenerating spent acid. For example, the present process may not require expensive facilities to conduct the multistages acid regeneration process. Further, the present process may be operated at ambient temperature and may not require expensive high-temperature equipment.

Another advantage of using the process according to embodiments disclosed herein is the reduced operating costs of regenerating spent acid. For example, the present process may be operated at ambient temperature, and therefore may be far less energy-intensive than the traditional process involving combustion of the spent sulfuric acid.

It is a further advantage of embodiments disclosed herein is that they may provide an economically acceptable method for the onsite regeneration of spent sulfuric acid.

Another advantage is that embodiments disclosed herein may provide an environmentally acceptable method for the onsite regeneration of spent sulfuric acid, as little or no combustion byproducts, including carbon dioxide, may be generated, compared to the traditional spent acid combustion process.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for regeneration of sulfuric acid, comprising:
   contacting a spent sulfuric acid comprising sulfuric acid and acid soluble oils with sulfur dioxide, wherein at least a portion of the acid soluble oils partitions into the sulfur dioxide;
   recovering an extract fraction comprising the sulfur dioxide and at least a portion of the acid soluble oils;
   recovering a raffinate fraction comprising the spent sulfuric acid, having a reduced content of the acid soluble oils.

2. The process according to claim 1, further comprising:
   separating the extract fraction to recover a first sulfur dioxide fraction and an acid soluble oils fraction; and
   separating the raffinate fraction to recover a second sulfur dioxide fraction and a sulfuric acid fraction.

3. The process according to claim 2, wherein at least one of the separating the raffinate fraction and the separating the extract fraction is performed in at least one of a distillation tower and a stripping tower.

4. The process according to claim 3, wherein the first sulfur dioxide fraction is recovered as an overheads fraction and the acid soluble oils fraction is recovered as a bottoms fraction.

5. The process according to claim 3, wherein the second sulfur dioxide fraction is recovered as an overheads fraction and the sulfuric acid fraction is recovered as a bottoms fractions.

6. The process according to claim 1, wherein the contacting is performed at conditions of temperature and pressure such that the sulfur dioxide is a liquid.

7. The process according to claim 1, wherein the sulfur dioxide and the spent sulfuric acid form a two-phase immiscible liquid-liquid system during the contacting.

8. The process according to claim 7, wherein the water content of the sulfur dioxide is less than 5 weight percent.

9. The process according to claim 7, wherein the water content of the spent sulfuric acid is less than 5 weight percent.

10. The process according to claim 2, further comprising:
    feeding sulfuric acid to an alkylation reaction zone;
    contacting the sulfuric acid with paraffins and olefins in the alkylation reaction zone to produce an alkylate product and a spent sulfuric acid comprising sulfuric acid and acid soluble oils;
    recovering the alkylate product as an alkylate product fraction;
    feeding at least a portion of the spent sulfuric acid as the spent sulfuric acid fraction for the contacting.

11. The process of claim 10, further comprising recycling at least a portion of the spent sulfuric acid fraction to the alkylation reaction zone.

12. The process according to claim 2, further comprising adding an inert gas to the raffinate fraction prior to the separating the raffinate fraction.

13. The process according to claim 12, wherein the inert gas comprises at least one of isobutane, propane and nitrogen.

14. The process according to claim 2, further comprising increasing a concentration of sulfuric acid in the sulfuric acid fraction by contacting at least a portion of the sulfur dioxide in at least one of the first sulfur dioxide fraction and the second sulfur dioxide fraction with oxygen in presence of a vanadium catalyst to produce sulfur trioxide, and contacting the sulfur trioxide with any water contained in the sulfuric acid fraction to produce additional sulfuric acid.

15. An alkylation process, comprising:
    contacting olefins and paraffins with sulfuric acid in an alkylation reaction zone;
    recovering an alkylate product from the alkylation reaction zone;
    recovering a spent sulfuric acid comprising sulfuric acid and acid soluble oils from the alkylation reaction zone;
    contacting at least a portion of the spent sulfuric acid with sulfur dioxide in an extraction zone, wherein at least a portion of the acid soluble oils partitions into the sulfur dioxide;
    recovering an extract fraction comprising the sulfur dioxide and at least a portion of the acid soluble oils from the extraction zone;
    recovering a raffinate fraction comprising the spent sulfuric acid, having a reduced content of acid soluble oils, from the extraction zone;
    separating the extract fraction in a first separation zone to recover a first sulfur dioxide fraction and an acid soluble oils fraction; and
    separating the raffinate fraction in a second separation zone to recover a second sulfur dioxide fraction and a sulfuric acid fraction.

16. The process according to claim 15, further comprising recycling at least a portion of the sulfuric acid fraction to the alkylation reaction zone.

17. The process according to claim 16, further comprising:
    contacting at least a portion of the sulfur dioxide in at least one of the first sulfur dioxide fraction and the second sulfur dioxide fraction with oxygen in presence of a vanadium catalyst to produce sulfur trioxide;
    contacting the sulfur trioxide with any water contained in the sulfuric acid fraction to produce additional sulfuric acid;
    recovering a concentrated sulfuric acid fraction comprising the additional sulfuric acid; and
    recycling at least a portion of the concentrated sulfuric acid fraction to the alkylation reaction zone.

18. The process according to claim 15, wherein the sulfur dioxide in the extraction zone is a liquid.

19. The process according to claim 15, wherein the sulfur dioxide and the spent sulfuric acid form a two-phase immiscible liquid-liquid system during the contacting.

* * * * *